United States Patent [19]
Bolonick et al.

[11] Patent Number: 5,863,910
[45] Date of Patent: Jan. 26, 1999

[54] TREATMENT OF CHRONIC INFLAMMATORY DISORDERS OF THE GASTROINTESTINAL TRACT

[76] Inventors: Joel Bolonick, 2435 College Ave., Apt. 12, Berkeley, Calif. 94704; Alan Stewart, 6840 Paso Robles Dr., Oakland, Calif. 94611

[21] Appl. No.: 955,269

[22] Filed: Oct. 21, 1997

Related U.S. Application Data

[63] Continuation of Ser. No. 585,680, Jan. 12, 1996, abandoned.
[51] Int. Cl.⁶ .................................................. A61K 31/58
[52] U.S. Cl. ............................................. 514/174
[58] Field of Search ............................................. 514/174

[56] References Cited

U.S. PATENT DOCUMENTS 5,674,860  10/1997  Carling et al. .

FOREIGN PATENT DOCUMENTS

| 725644 B1 | 6/1995 | European Pat. Off. . |
| 0794767 B1 | 7/1996 | European Pat. Off. . |
| WO95/08323 | 3/1995 | WIPO . |
| WO96/19969 | 7/1996 | WIPO . |
| WO98/00111 | 1/1998 | WIPO . |
| WO98/13031 | 4/1998 | WIPO . |

OTHER PUBLICATIONS

Gennaro et al., eds., "Capsules", *Remington's Pharmaceutical Sciences*, 18th ed., 1658–1664 (1990).

Greenberg et al., "Oral Budesonide for Active Crohn's Disease", *The New England Journal of Medicine*, 331(13) : 836–841 (1994).

Löfberg et al., "Budesonide versus prednisolone retention enemas in active distal ulcerative colitis", *Alimentary Pharmacology and Therapeutics*, 8 (6) :623–629 (1994).

Reynolds and Hunter, "Pharmacotheraphy of Imflammatory Bowel Disease", *Dig. Dis.*, 11:334–342 (1993).

Rutgeerts et al., "A Comparison of Budesonide with Prednisolone for Active Crohn's Disease", *The New England Journal of Medicine*, 331(13) :842–845 (1994).

Spencer and McTavish, "Budesonide: A Review of its Pharmacological Properties and Tharapeutic Efficacy in Inflammatory Bowel Disease", *Drugs*, 50 (5) :854–872 (1995).

Ishihara, *Biological Abstracts*, vol. 72, No. 6, abstract No. 40363, 1981.

*Primary Examiner*—William R. A. Jarvis
*Attorney, Agent, or Firm*—Nixon & Vanderhye

[57] ABSTRACT

The present disclosure relates to an oral formulation for treating gastrointestinal inflammation that includes an effective amount of budesonide suspended in an edible oil, typically a vegetable oil. A method for treating gastrointestinal inflammation in mammals is also described and includes orally administering a composition of this invention to a mammal. In one embodiment, an initial dosage is administered daily for about two to four weeks and the dosage is subsequently tapered, generally at about two week intervals, in response to a reduction in symptoms until a minimum dose that controls symptoms is achieved.

19 Claims, No Drawings

TREATMENT OF CHRONIC INFLAMMATORY DISORDERS OF THE GASTROINTESTINAL TRACT

This application is a continuation of application Ser. No. 08/585,680, filed Jan. 12, 1996 now abandoned.

BACKGROUND OF THE INVENTION

1. Field of the Invention

The present invention relates to a composition and method for treatment of chronic inflammatory disorders of the gastrointestinal tract in mammals.

2. Prior Art

Chronic inflammatory disorders of the gastrointestinal tract are generally grouped under the heading of inflammatory bowel disease, although the disease can affect any part of the gastrointestinal tract from the esophagus to the large intestine. Inflammatory bowel disease is of unknown etiology, although psychological, immunologic, and genetic sources have been discussed as possible etiologic factors. The gastrointestinal inflammation associated with inflammatory bowel disease causes a range of symptoms of increasing severity and with a variety of intestinal and extraintestinal manifestations.

The manifestations of chronic inflammatory bowel disease range from mild to very severe, the more severe including colitis, characterized by an inflammatory reaction involving primarily the colonic mucosa, and Crohn's disease, characterized by inflammation throughout the gastrointestinal tract. The clinical features of ulcerative colitis and Crohn's disease can be similar. Characteristic symptoms include abdominal pain, straining, diarrhea with or without blood, fatigue, fever, and weight loss. Even the mildest of these conditions can carry obvious emotional and psychological burdens. The quality of life of an affected individual can be significantly reduced.

Methods of treatment of inflammatory bowel disease generally involve drug therapy directed towards the suppression of gastrointestinal inflammation. Of the anti-inflammatory drugs, adrenal corticosteroids such as prednisone and prednisolone have been found to be the most efficacious treatment of Crohn's disease and ulcerative colitis. However, the effectiveness of corticosteroids in relieving the symptoms of gastrointestinal inflammation is often accompanied by unfortunate steroid side effects, including hair loss, increased water and food intake, weight gain, and immunosuppression. These systemic side effects can develop after even short-term treatment. Thus, a treatment that is effective in controlling the symptoms of gastrointestinal inflammation but with minimal systemic effects has been sought.

Recent investigations have studied the efficacy of budesonide, a corticosteroid analogue with low systemic bioavailability, as a treatment for inflammatory bowel disease. Budesonide has been found to be efficacious when used as an enema to treat colitis. [Lofberg et al., *Alimentary Pharmacology and Therapeutics*, 8(6):623–629 (1994).] The drug has also been used in clinical trials as a treatment for Crohn's disease. Administered in place of a corticosteroid such as prednisone or prednisolone, budesonide minimizes systemic side effects associated with corticosteroid treatment.

A recent clinical trial [Rutgeerts et al., *The New England Journal of Medicine*, 331(13):842–845 (1994)] compared the efficacies and safeties of prednisolone and budesonide in treating Crohn's disease. Granular budesonide was administered in a controlled-release capsule directed for ileal release in a dosage of 9 mg per day for eight weeks and then 6 mg per day for two weeks. The subjects treated with budesonide demonstrated fewer systemic side effects and less adrenal-suppression than those treated with prednisolone. However, budesonide was found to be less efficacious than prednisolone in reducing the symptoms of Crohn's disease.

In another clinical trial investigating the safety and efficacy of budesonide in treating Crohn's disease [Greenberg et al., *The New England Journal of Medicine* 331(13):836–841 (1994)], groups of subjects received two daily dosages totalling 3, 9, or 15 mg of budesonide per day. The dosage was administered in a formulation of microgranules of budesonide contained in a controlled-ideal-release gelatin capsule. Greenberg et al. found 9 mg to be the lowest effective dose for induction of remission of Crohn's disease. Greenberg et al. additionally found that at such a dose steroid-related side effects, though less severe than those associated with prednisone, were present in a significant proportion of the subjects.

A treatment effective both in treating gastrointestinal inflammation and in reducing the systemic side effects associated with corticosteroid treatment is still being sought.

SUMMARY OF THE INVENTION

The present invention provides an oral formulation for treating gastrointestinal inflammation that includes an effective amount of budesonide suspended in an edible oil, typically a vegetable oil such as avocado oil. In an embodiment of the invention, the suspension of budesonide is encapsulated in a controlled-release coating for release in a specific portion of the gastrointestinal tract.

A method for treating gastrointestinal inflammation in mammals is also provided. The method includes orally administering a composition of this invention to the mammal. In one embodiment, an initial dosage is administered daily for about two to four weeks and the dosage is subsequently tapered, generally at about two week intervals, in response to a reduction in symptoms. The reduction in dosage can be from about ⅓ to about ½ of the initial dosage until a minimum dose that controls symptoms is determined.

DETAILED DESCRIPTION OF THE INVENTION

The present invention provides an oral formulation of budesonide for treatment of gastrointestinal inflammation. The formulation effectively controls the symptoms of inflammatory bowel disease at a lower dosage than the prior art formulations, thus minimizing the side effects associated with corticosteroid treatment. A method of treatment is also provided.

An oral formulation of this invention for treating gastrointestinal inflammation includes an effective amount of budesonide suspended in an edible oil. The terms "gastrointestinal inflammation", "inflammatory bowel disease", and "inflammation of the gastrointestinal tract" are used interchangeably herein to mean inflammation of any portion of the gastrointestinal tract, from the esophagus to the sigmoid flexure or the termination of the colon in the rectum. The inflammation can be acute, but, generally, the composition of this invention is used to treat chronic conditions.

Budesonide is a corticosteroid manufactured by Astra Draco (Lund, Sweden). Budesonide is commercially available as a granular powder that can be suspended in an oil without further processing. However, additional processing to ensure that all particles are of a suitably small size for preparation of a suspension can be performed. Such processing can include sieving of the granules to obtain those of the desired size or further powdering or milling to minimize the presence of larger granules.

The budesonide is suspended in an edible oil. Any edible oil is suitable for use in the formulation. In general, the oil is liquid at room temperature and somewhat below room temperature. Conveniently, the oil is a vegetable oil. However, fish oils and other edible animal oils also can be used. Suitable edible oils include those vegetable oils that are recommended for dietary uses such as corn, safflower, olive, and avocado oils, and mixtures of such oils. The oil can be selected to comport with any specific dietary guidelines. Polyunsaturated oils are preferred. When the suspension is administered to the animal to be treated by placing the suspension on the food or in a food dish, an oil that is palatable to the animal, such as avocado oil, is conveniently used. The palatability of the oil is not of concern when the suspension is administered in an encapsulated form.

Budesonide is present in the formulation in an effective amount. The amount needed for effective treatment varies depending on numerous well known factors such as the severity and chronicity of the disease, the species, histopathologic type, and weight of the treated animal, the length and course of treatment, the region of the gastrointestinal tract to be treated, and the responsiveness of the treated animal. Determination of an effective dose is described in detail hereinafter.

Conveniently, budesonide is suspended in the oil at a concentration of about 1 mg/ml to about 2 mg/ml. Such concentrations are suitable for administration of typical dosages required for treatment of humans and domestic animals, such as dogs and cats. The suspension is relatively viscous at concentrations much above 2 mg/ml. Therefore, concentrations at 2 mg/ml or less are more suitable for ease of administration. This is less of a concern when the formulation is encapsulated. At concentrations much below 1 mg/ml, larger volumes of the suspension need to be administered to achieve the effective dose for larger animals, such as large dogs or humans. Therefore, concentrations of about 1 mg/ml to about 2 mg/ml are convenient for administration and formulation of an effective dose.

In addition, such concentrations of budesonide also are capable of being formulated as stable colloidal suspensions. In particular, colloidal suspensions of budesonide at 1 mg/ml in various vegetable oils were stable at room temperature for at least four months in that no precipitation of budesonide was observed.

The suspension can be encapsulated in a controlled-release coating, conveniently for release in the affected organ when the inflammation is localized to a particular region of the gastrointestinal tract. A controlled-release formulation directed for release in a specific portion of the gastrointestinal tract permits localized exposure to budesonide and reduces unnecessary exposure of other portions of the gastrointestinal tract to the drug, further minimizing side effects. Even when the target organ is the stomach, use of an enteric coating is beneficial in eliminating exposure of the mouth and esophagus to the drug and thus minimizing side effects. The controlled-release capsules can conveniently be formulated to contain total amounts of budesonide for ease of administration to the intended mammal. For example, capsules convenient for use in treatment of humans can contain dosages of 3 mg, 6 mg, or 9 mg of budesonide.

The method of treatment of the present invention includes oral administration of a suspension of budesonide in edible oil to a mammal. As represented in the present application, the mammal can be a human, dog, or cat. In addition, the method is also suitable for treatment of commercially valuable mammals, including domestic animals such as horses, pigs, cattle, and sheep, and rare and exotic mammals such as those in zoos.

The proper dosage and an appropriate dosage regimen varies depending on numerous well known factors such as the severity and chronicity of the disease, the species, histopathologic type, and weight of the treated animal, the length and course of treatment, the region of the gastrointestinal tract to be treated, and the sensitivity of the treated animal to corticosteroid treatment. For example, in cats, gastrointestinal disorders often include stomach and duodenal involvement. In dogs, gastrointestinal disorders mostly effect the small and large intestine, while in humans ileal and bowel involvement is most common. Since the sensitivity of humans to corticosteroids is similar to that of dogs, appropriate dosage ratios for treatment of gastrointestinal inflammation in humans can be extrapolated from the dosages suitable for treatment of gastrointestinal inflammation in dogs.

Cats are as responsive to treatment with corticosteroids as dogs, but experience fewer side effects. In general, the initial dose for cats is about four times that for dogs. More specifically, cats were started on an initial dose of 0.2 mg/kg twice a day and tapered to a usual maintenance dose of 0.1 mg/kg administered every other day. Dogs were started on an initial dose of 0.05 mg/kg twice a day and tapered according to response to be drug free or maintained at a dose of 0.05 mg/kg administered every other day. Although the daily dosage was conveniently administered in two portions, a single dose of twice the amount can also be used. The dose in humans is similar to that in dogs.

To determine starting doses for other mammals, a comparison of the relative doses of other corticosteriods can be used. In particular, the potency of budesonide is about 10–20 times that of prednisolone. A typical dosage of budesonide in oil should thus generally be about 1/10 to 1/20 that of the dosage of prednisone or prednisolone expected to be suitable for the particular animal. Determination of initial and maintenance doses is described more fully below.

As is well known in treating gastrointestinal inflammation, in general, a relatively large initial dose is given, usually for a period of two to four weeks or longer depending on the severity of the disease. In particular, a portion of the initial dose of drug fails to be absorbed due to uncontrolled diarrhea. As the symptoms of the disease are alleviated by the portion of the drug that is absorbed, the full effect of the drug becomes apparent. Then the dose is generally reduced, usually to about one-half of the initial dose for a period of an additional two weeks to four weeks.

However, smaller reductions, such as by one-third, can also be used, particularly after one or more reductions in dose have been instituted. If the reduced dose does not lead to the return of symptoms, the dose can be further reduced. If the symptoms return, the earlier dose can be repeated, then reduced by a smaller fraction. If the reduced dose is effective for two to four weeks, a further reduction in dosage can be attempted. As is well known, each dose must be administered for a period of a week or more because a high dose can control symptoms for days after the drug is withdrawn. Preferably, each dose following the initial dose is given for at least about two weeks.

To determine the efficacy of a dose of the drug clinically, the intestines are palpated to determine if they are thickened or if the palpation causes or aggravates discomfort. The two keys to determining that symptoms are effectively controlled that can be asked of a patient or readily determined by the owner of an animal are the presence of a firm stool and the absence of vomiting or discomfort.

The treatment of gastrointestinal inflammation is idiosyncratic and adjustment of dosages of corticosteroids is well within the level of skill. However, usually the disease comes in cycles having periods of elevated symptoms at the early stages. Often, the disease is aggravated by periods of stress at any stage of the disease. In the early stages, symptoms are often intermittent, and administering an effective form of therapy may be difficult. Later, the cycles tend to cease, and the symptoms are present consistently. Often a maintenance dose must be administered daily in the later stages of the disease.

The formulation of this invention is prepared by well known methods. In particular, budesonide is suspended in an edible oil by adding the amount of budesonide necessary for the desired concentration to the selected oil and shaking or otherwise admixing the preparation until a suspension is achieved. Usually, the suspension is a stable colloidal suspension. In particular, a colloidal suspension can be prepared by hand or mechanical shaking of the drug in oil for a period of two minutes for a concentration of 1 mg/ml without any initial processing of budesonide as obtained from the manufacturer. The suspension appears stable once it is prepared and requires no special storage.

Once the suspension is prepared, it can be encapsulated by standard techniques. Techniques for encapsulation are well known and are described in *Remington's Pharmaceutical Sciences* [Gennaro et al., eds., *Remington's Pharmaceutical Sciences*, 18th ed., 1658–1664 (1990)]. In addition, formulations for enteric release of budesonide are described in Greenberg et al., *The New England Journal of Medicine* 331(13):836–841 (1994); Rutgeerts et al., *The New England Journal of Medicine,* 331(13):842–845 (1994); and Reynolds et al., *Digestive Diseases,* 11:334–342 (1993).

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. Examples set forth in the past tense have been actually reduced to practice. Examples set forth in the present tense are constructively reduced to practice. All literature citations herein are expressly incorporated by reference.

EXAMPLE 1

A clinical trial of the formulation of this invention for treatment of gastrointestinal inflammation was performed at a veterinary hospital. The study was conducted on dogs and cats with inflammations of the gastrointestinal tract which were diagnosed as forms of inflammatory bowel disease using endoscopy and biopsy. The study was performed as described below.

Formulation

The formulation was powdered budesonide (Sigma Chemical Company; St. Louis, Mo.; Catalog No. B-7777) suspended in either avocado oil or safflower oil at a concentration of 1 mg/ml. The avocado oil was chosen originally because of its palatability to cats. However, one cat developed a sensitivity to avocado oil and safflower oil was substituted. The drug was weighed out in small quantities (approximately 40 mg), added to a centrifuge tube, and sufficient oil (for 40 ml total volume) was added to make the desired concentration of 1 mg/ml.

The tube was then vigorously shaken until all the material was completely suspended. On standing, a small percentage of the total material may have settled out and required additional shaking to resuspend. This was attributed to the variation in size of particles in the original powder, with the heavier particles not entering a truly colloidal phase. In general, not more than about 5% of the powdered budesonide settled out after the initial suspension was prepared.

Delivery

Cats were started on an initial dose of 0.2 mg/kg twice a day. The dose was tapered according to the response, usually being maintained at 0.1 mg/kg every other day. The dosages were tapered after two to four weeks. Dogs were started at 0.05 mg/kg twice a day. The dose was also tapered according to response, the animals ultimately being maintained drug free or on a dose of 0.05 mg/kg every other day. The suspension was administered to animals either directly into the mouth via a syringe or by simply allowing the animal to eat a measured amount of the drug alone or with food.

Clinical Data

The clinical trial of the formulation was begun with a single cat having severe inflammatory gastric and intestinal disease. By about seven months later, a total of 2 dogs and 8 cats had been enrolled in the study. All animals had previously been medicated with prednisone or prednisolone. The average starting dose for prednisone or prednisolone was 1 mg/kg orally twice a day, which was tapered depending on the animal's response.

The animals were chosen for the budesonide oil suspension study based on one or more of the following reasons: insufficient control of symptoms by prednisolone; side effects of prednisolone; and concurrent diseases making the use of systemic steroids undesirable, including diabetes, immunosuppression, viral infections, and pancreatitis.

Once begun on the budesonide oil suspension formulation, all animals remained under observation for at least six months, except for a single cat which was euthanized for unrelated reasons by another veterinary clinic. The shortest period of treatment was 2 months and the longest was 6 months. A questionnaire was sent to the owners of all animals on the drug, following about 4 months in the study. The questionnaire requested information regarding the treatment. The questionnaire included both objective criteria (frequency of vomiting, and quality of stool), and more subjective criteria (ease of administration, appetite, energy level, and overall comfort). The pets' owners were asked to rate the budesonide in oil suspension treatment in comparison to prior treatment with prednisolone and in comparison to no treatment and to rate use of prednisolone in comparison to no treatment, rating the treatment from much worse to much improved. More specifically, the treatment was rated as much worse (scored as −3); moderately worse (scored as −2); slightly worse (scored as −1); no change (scored as 0); slightly improved (scored as 1); moderately improved (scored as 2); and much improved (scored as 3).

The average scores for each category were tabulated. The results are illustrated below in Table 1.

TABLE 1

| Category | prednisolone vs no drug | budesonide vs no drug | budesonide vs prednisolone |
|---|---|---|---|
| ease of administration | NA* | NA* | 2.0 |
| overall comfort | 0.0 | 2.2 | 2.1 |
| frequency of vomiting | 1.2 | 1.9 | 1.2 |
| quality of stool | 0.6 | 1.8 | 1.7 |
| energy level | -0.1 | 1.6 | 1.9 |
| appetite | 0.0 | 1.5 | 1.6 |

*NA: Not applicable (information was not requested)

Based on the scores, it is apparent that the budesonide formulation was a significant improvement over prednisone and prednisolone for the treatment of inflammatory bowel disease in dogs and cats. This improvement was attributed to both greater potency of the formulation and fewer associated side effects.

The study determined that the formulation of a suspension of budesonide in an edible oil provides not only noticeably diminished side-effects over prednisolone but also superior efficacy for the control of the disease over both prednisolone and budesonide when formulated as other than an oil suspension.

EXAMPLE 2

Alternate formulations were tried on one cat and one dog with much poorer results than the vegetable oil formulation. One formulation was budesonide (also at 1 mg/ml) suspended in 40% glycerol, 60% water. Another vehicle was 10% polyethylene glycol (molecular weight 800) and 90% water with budesonide suspended at 1 mg/ml. In both cases the budesonide appeared to be evenly suspended, creating a milky white suspension. However, both formulations were so inferior in efficacy to the vegetable oil formulation that it was judged improper to continue and the animals were treated as described in Example 1.

What is claimed is:

1. An oral formulation for treating gastrointestinal inflammation comprising a suspension of an effective amount of budesonide in an edible oil derived from an animal or vegetable.

2. The oral formulation of claim 1 wherein budesonide is present at a concentration of about 1.0 to 2.0 mg/ml.

3. The oral formulation of claim 1 wherein the suspension is a colloidal suspension.

4. The oral formulation of claim 1 wherein the edible oil is a polyunsaturated oil.

5. The oral formulation of claim 1 wherein the edible oil is a vegetable oil.

6. The oral formulation of claim 5 wherein the vegetable oil is selected from the group consisting of avocado oil, olive oil, and safflower oil.

7. The oral formulation of claim 1 wherein the suspension is encapsulated in a controlled-release coating.

8. The oral formulation of claim 7 wherein the controlled-release coating is formulated for release in the small intestine.

9. The oral formulation of claim 7 wherein the controlled-release coating is formulated for release in the large intestine.

10. The oral formulation of claim 7 wherein the controlled-release coating is formulated for release in the stomach.

11. A method for treating gastrointestinal inflammation in a mammal comprising orally administering a suspension comprising an effective amount of budesonide in an edible oil to the mammal.

12. The method of claim 11 wherein the suspension is administered daily for at least four weeks.

13. The method of claim 11 wherein the mammal is a dog and an initial dosage of 0.1 mg/kg of budesonide is administered daily.

14. The method of claim 11 wherein the mammal is a cat and an initial dosage of 0.4 mg/kg of budesonide is administered daily.

15. The method of claim 11 wherein the mammal is a human and an initial dosage of 0.1 mg/kg of budesonide is administered daily.

16. The method of claim 11 wherein an initial dosage is administered twice daily for about two to four weeks and subsequently reduced in response to a reduction in symptoms.

17. The method of claim 16 wherein the dosage is subsequently reduced by about one-third to one-half of the initial dosage.

18. The oral formulation of claim 1 wherein said formulation is substantially free of water.

19. The method of claim 11 wherein said suspension is substantially free of water.

* * * * *